(12) United States Patent
Desai et al.

(10) Patent No.: US 8,765,409 B2
(45) Date of Patent: *Jul. 1, 2014

(54) EFFICIENT PRODUCTION OF HETEROLOGOUS PROTEINS USING MANNOSYL TRANSFERASE INHIBITORS

(75) Inventors: Ranjit Desai, Kendall Park, NJ (US); Lihu Yang, Edison, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 1 day.

This patent is subject to a terminal disclaimer.

(21) Appl. No.: 13/588,022

(22) Filed: Aug. 17, 2012

(65) Prior Publication Data

US 2013/0316398 A1 Nov. 28, 2013

Related U.S. Application Data

(63) Continuation of application No. 12/993,716, filed as application No. PCT/US2009/044297 on May 18, 2009, now Pat. No. 8,309,325.

(60) Provisional application No. 61/128,251, filed on May 20, 2008.

(51) Int. Cl.
*C12P 21/00* (2006.01)
*C07D 277/36* (2006.01)

(52) U.S. Cl.
USPC .................................... 435/69.1; 548/183

(58) Field of Classification Search
USPC ................. 435/69.1, 71.1; 548/183
See application file for complete search history.

(56) References Cited

U.S. PATENT DOCUMENTS

| 6,103,501 A | 8/2000 | Boime et al. |
| 6,506,755 B2 | 1/2003 | Friebe et al. |
| 6,589,995 B2 | 7/2003 | Konrad et al. |
| 6,740,670 B2 | 5/2004 | Orchard et al. |
| 6,794,401 B2 | 9/2004 | Nag et al. |
| 7,034,021 B2 | 4/2006 | Moinet et al. |
| 7,071,218 B2 | 7/2006 | Pfahl et al. |
| 7,102,000 B2 | 9/2006 | Pfahl et al. |
| 7,105,554 B2 | 9/2006 | Orchard et al. |
| 7,268,364 B2 | 9/2007 | Koch et al. |
| 7,332,631 B2 | 2/2008 | Hogarth et al. |
| 7,452,883 B2 | 11/2008 | Moinet et al. |
| 7,521,465 B2 | 4/2009 | Nag et al. |
| 7,767,676 B2 | 8/2010 | Moinet et al. |
| 7,781,464 B2 | 8/2010 | Neogi et al. |
| 8,309,325 B2 * | 11/2012 | Desai et al. .................. 435/69.1 |
| 2003/0186948 A1 | 10/2003 | Kudlow et al. |
| 2008/0051445 A1 | 2/2008 | Surolia et al. |
| 2009/0191587 A1 | 7/2009 | Chiba et al. |
| 2010/0099726 A1 | 4/2010 | Cantley et al. |

FOREIGN PATENT DOCUMENTS

| EP | 2022855 A | 2/2009 |
| JP | 2007045014 | 2/2007 |
| JP | 2007045946 | 2/2007 |
| WO | 9429287 | 12/1994 |
| WO | 0217915 | 3/2002 |
| WO | 03070238 | 8/2003 |
| WO | WO03/070239 | 8/2003 |
| WO | 2004058747 | 7/2004 |
| WO | 2006109146 | 10/2006 |
| WO | 2007061631 | 5/2007 |
| WO | 2007132949 | 11/2007 |

OTHER PUBLICATIONS

Orchard, et al., Bioorg. Med. Chem. Lett. (2004) 14, 3975-3978.
Bursavich, et al., Bioorg. Med. Chem. Lett. (2007) 17, 1185-1188.

* cited by examiner

*Primary Examiner* — Kristin Vajda

(57) ABSTRACT

Compounds and methods are described for producing protein compositions having reduced amounts of O-linked glycosylation. The method includes producing the protein in cells cultured in the presence of certain benzylidene thiazolidinediones inhibitors of Pmt-mediated O-linked glycosylation.

15 Claims, 1 Drawing Sheet

EFFICIENT PRODUCTION OF HETEROLOGOUS PROTEINS USING MANNOSYL TRANSFERASE INHIBITORS

This application is a continuation of U.S. application Ser. No. 12/993,716, filed Nov. 19, 2010, now pending, which is a 371 of International Patent Application No PCT/US2009/044297, which claims the benefit of U.S. Provisional Patent Application No. 61/128,251, filed May 20, 2008.

REFERENCE TO SEQUENCE LISTING SUBMITTED ELECTRONICALLY

The sequence listing of the present application is submitted electronically via EFS-Web as an ASCII formatted sequence listing with a file name "MRL-BIO-22560_SEQLIST.txt. This sequence listing submitted via EFS-Web is part of the specification and is herein incorporated by reference in its entirely.

BACKGROUND OF THE INVENTION

Glycoproteins mediate many essential functions in humans and other mammals, including catalysis, signaling, cell-cell communication, and molecular recognition and association. Glycoproteins make up the majority of non-cytosolic proteins in eukaryotic organisms (Lis Sharon, 1993, Eur. J. Biochem. 218:1-27). Many glycoproteins have been exploited for therapeutic purposes, and during the last two decades, recombinant versions of naturally-occurring glycoproteins have been a major part of the biotechnology industry. Examples of recombinant glycosylated proteins used as therapeutics include erythropoietin (EPO), therapeutic monoclonal antibodies (mAbs), tissue plasminogen activator (tPA), interferon-β (IFN-β), granulocyte-macrophage colony stimulating factor (GM-CSF), and human chorionic gonadotrophin (hCH) (Cumming et al., 1991, Glycobiology 1:115-130). Variations in glycosylation patterns of recombinantly produced glycoproteins have recently been the topic of much attention in the scientific community as recombinant proteins produced as potential prophylactics and therapeutics approach the clinic.

In general, the glycosylation structures of glycoprotein oligosaccharides will vary depending upon the host species of the cells used to produce them. Therapeutic proteins produced in non-human host cells are likely to contain non-human glycosylation which may elicit an immunogenic response in humans—e.g. hypermannosylation in yeast (Ballou, 1990, Methods Enzymol. 185:440-470); α(1,3)-fucose and β(1,2)-xylose in plants, (Cabanes-Macheteau et al., 1999. Glycobiology, 9: 365-372); N-glycolylneuraminic acid in Chinese hamster ovary cells (Noguchi et al., 1995. J. Biochem. 117: 5-62); and, Galα-1,3Gal glycosylation in mice (Borrebaeck, et ad., 1993, Immun. Today, 14: 477-479). Carbohydrate chains bound to proteins in animal cells include N-glycoside bond type carbohydrate chains (also called N-glycans; or N-linked glycosylation) bound to an asparagine (Asn) residue in the protein and O-glycoside bond type carbohydrate chains (also called O-glycans; or O-linked glycosylation) bound to a serine (Ser) or threonine (Thr) residue in the protein.

Because the oligosaccharide structures of glycoproteins produced by non-human mammalian cells tend to be more closely related to those of human glycoproteins, most commercial glycoproteins are produced in mammalian cells. However, mammalian cells have several important disadvantages as host cells for protein production. Besides being costly, processes for producing proteins in mammalian cells produce heterogeneous populations of glycoforms, have low volumetric titers, and require both ongoing viral containment and significant time to generate stable cell lines.

It is well recognized that the particular glycoforms on a protein can profoundly affect the properties of the protein, including its pharmacokinetic, pharmacodynamic, receptor-interaction, and tissue-specific targeting properties (Graddis et al., 2002. Curr Pharm Biotechnol. 3: 285-297). For example, it has been shown that different glycosylation patterns of Igs are associated with different biological properties (Jefferis and Lund, 1997, Antibody Eng. Chem. Immunol., 65; 111-128; Wright and Morrison, 1997, Trends Biotechnol., 15: 26-32). It has further been shown that galactosylation of a glycoprotein can vary with cell culture conditions, which may render some glycoprotein compositions immunogenic depending on the specific galactose pattern on the glycoprotein (Patel et al., 1992. Biochem J. 285: 839-845). However, because it is not known which specific glycoform(s) contribute(s) to a desired biological function, the ability to enrich for specific glycoforms on glycoproteins is highly desirable. Because different glycoforms are associated with different biological properties, the ability to enrich for glycoproteins having a specific glycoform can be used to elucidate the relationship between a specific glycoform and a specific biological function of the glycoprotein. Also, the ability to enrich for glycoproteins having a specific glycoform enables the production of therapeutic glycoproteins having particular specificities. Thus, production of glycoprotein compositions that are enriched for particular glycoforms is highly desirable.

While the pathway for N-linked glycosylation has been the subject of much analysis, the process and function of O-linked glycosylation is not as well understood. However, it is known that in contrast to N-linked glycosylation, O-glycosylation is a posttranslational event, which occurs in the cis-Golgi (Varki, 1993, Glycobiol., 3: 97-130). While a consensus acceptor sequence for O-linked glycosylation like that for N-linked glycosylation does not appear to exist, a comparison of amino acid sequences around a large number of O-linked glycosylation sites of several glycoproteins show an increased frequency of proline residues at positions −1 and +3 relative to the glycosylated residues and a marked increase of serine, threonine, and alanine residues (Wilson et al., 1991, Biochem. J., 275: 529-534). Stretches of serine and threonine residues in glycoproteins, may also be potential sites for O-glycosylation.

One gene family that has a role in O-linked glycosylation are the genes encoding the Dol-P-Man:Protein (Ser/Thr) Mannosyl Transferase (Pmt). These highly conserved genes have been identified in both higher eukaryotes such as humans, rodents, insects, and the like and lower eukaryotes such as fungi and the like. Yeast such as *Saccharomyces cerevisiae* and *Pichia pastoris* encode up to seven PMT genes encoding Pmt homologues (reviewed in Willer et al. Curr. Opin. Struct. Biol. 2003 October; 13(5): 621-30.). In yeast, O-linked glycosylation starts by the addition of the initial mannose from dolichol-phosphate mannose to a serine or threonine residue of a nascent glycoprotein in the endoplasmic reticulum by one of the seven O-mannosyl transferases genes. While there appear to be seven PMT genes encoding Pmt homologues in yeast, O-mannosylation of secreted fungal and heterologous proteins in yeast is primarily dependent on the genes encoding Pmt1 and Pmt2, which appear to function as a heterodimer. PMT1 and PMT2 and their protein products, Pmt1 and Pmt2, respectively, appear to be highly conserved among species.

Tanner et al. in U.S. Pat. No. 5,714,377 describes the PMT1 and PMT2 genes of *Saccharomyces cerevisiae* and a method for making recombinant proteins having reduced O-linked glycosylation that uses fungal cells in which one or more of PMT genes have been genetically modified so that recombinant proteins are produced, which have reduced O-linked glycosylation.

Ng et al. in U.S. Published Patent Application No. 20020068325 discloses inhibition of O-glycosylation through the use of antisense or cosuppression or through the engineering of yeast host strains that have loss of function mutations in genes associated with O-linked glycosylation, in particular, one or more of the PMT genes.

UDP-N-acetyl-alpha-D-galactosamine:polypeptide N-acetyl galactosaminyl-transferases (GalNAc-transferases) are involved in mucin type O-linked glycosylation found in higher eukaryotes. These enzymes initiate O-glycosylation of specific serine and threonine amino acids in proteins by adding N-acetylgalactosamine to the hydroxy group of these amino acids to which mannose residues can then be added in a step-wise manner. Clausen et al. in U.S. Pat. No. 5,871,990 and U.S. Published Patent Application No. 20050026266 discloses a family of nucleic acids encoding UDP-N-acetyl-alpha-D-galactosamine:polypeptide N-acetyl galactosaminyl-transferases (GalNAc-transferases). Clausen in U.S. Published Patent Application No. 20030186850 discloses the use of GalNAc-beta-benzyl to selectively inhibit lectins of polypeptide GalNAc-transferases and not serve as substrates for other glycosyltransferases involved in O-glycan biosyntheses, thus inhibiting O-glycosylation.

Inhibitors of O-linked glycosylation have been described. For example, Orchard et al. in U.S. Pat. No. 7,105,554 describes benzylidene thiazolidinediones and their use as antimycotic agents, e.g., antifungal agents. These benzylidene thiazolidinediones are reported to inhibit the Pmt1 enzyme, preventing the formation of the O-linked mannoproteins and compromising the integrity of the fungal cell wall. The end result is cell swelling and ultimately death through rupture.

Konrad et al. in U.S. Published Patent Application No. 20020128235 disclose a method for treating or preventing diabetes mellitus by pharmacologically inhibiting O-linked protein glycosylation in a tissue or cell. The method relies on treating a diabetic individual with (Z)-1-[N-(3-Ammoniopropyl)-N-(n-propyl)amino]diazen-ium-1,2-diolate or a derivative thereof, which binds O-linked N-acetylglucosamine transferase and thereby inhibits O-linked glycosylation.

Kojima et al. in U.S. Pat. No. 5,268,364 disclose therapeutic compositions for inhibition of O-glycosylation using compounds such as benzyle-α-N-acetylgalactosamine, which inhibits extension of O-glycosylation leading to accumulation of O-α-GalNAc, to block expression of SLex or SLea by leukocytes or tumor cells and thereby inhibit adhesion of these cells to endothelial cells and platelets.

Boime et al. U.S. Pat. No. 6,103,501 disclose variants of hormones in which O-linked glycosylation was altered by modifying the amino acid sequence at the site of glycosylation.

The invention is directed to novel inhibitors of Pmt proteins, which are useful for production of recombinant proteins with reduced O-linked glycosylation. This enables O-linked glycosylation of proteins produced from fungi and yeast cells to be controlled.

SUMMARY OF THE INVENTION

Compounds and methods are described for producing protein compositions having reduced amounts of O-linked glycosylation. The method includes producing the protein in cells cultured in the presence of certain benzylidene thiazolidinediones inhibitors of Pmt-mediated O-linked glycosylation.

DETAILED DESCRIPTION OF THE INVENTION

Figure 1A:
FIG. 1 illustrates the effect of Pmt inhibitors including the novel inhibitor shown as Example 4 on O-glycosylation of secreted recombinant monoclonal antibody in *Pichia pastoris*. The chemical inhibitors of Pmt reduced O-glycosylation in a dose-dependent fashion. Western blotting using an anti-human H+L antibody was used to detect heavy (Hc) and light (Lc) chains in the growth media of strains treated with increasing amounts of Pmt inhibitor (higher doses in left lanes). The slowest migrating band (marked with asterisk) indicates the O-glycosylated Hc which is eliminated by Pmt inhibitor treatment.

The present invention provides novel compounds and methods for expressing a recombinant protein (includes polypeptides and glycoproteins), which is susceptible to O-linked glycosylation in a particular host cell, having a reduced amount of O-linked glycosylation (including no O-linked glycosylation) in that cell type. The method involves inducing expression of a protein of interest in a host cell in which the protein is susceptible to O-linked glycosylation in the host cell in the presence of one or more novel compounds of the invention which are inhibitors of the activity of one or more of the Dol-P-Man:Protein (Ser/Thr) Mannosyl Transferase (Pmt) proteins involved in the transfer of mannose to a serine or threonine residue of the protein in the cell, optionally with one or more a 1,2-mannosidases as described in Bobrowicz et al. U.S. Published Application No. 2007061631, at the time expression of the protein is induced. The protein that is expressed in the presence of the inhibitor has a reduced amount of O-linked glycosylation compared to the amount of O-linked glycosylation that would have been present on the protein if it had been produced in the absence of the inhibitor. The method is particularly useful because it provides a means for producing therapeutically relevant proteins where it is desired that the protein have a reduced amount of O-glycosylation in host cells such as lower eukaryotes, for example yeast, and bacteria, which would normally produce proteins with O-linked glycans, having a reduced number of O-linked glycans. However, while the method is especially suitable for expressing proteins with reduced O-linked glycosylation in lower eukaryotic organisms, the method can also be practiced in higher eukaryotic organisms and bacteria.

The Pmt inhibitors of the invention are selected from the following group:

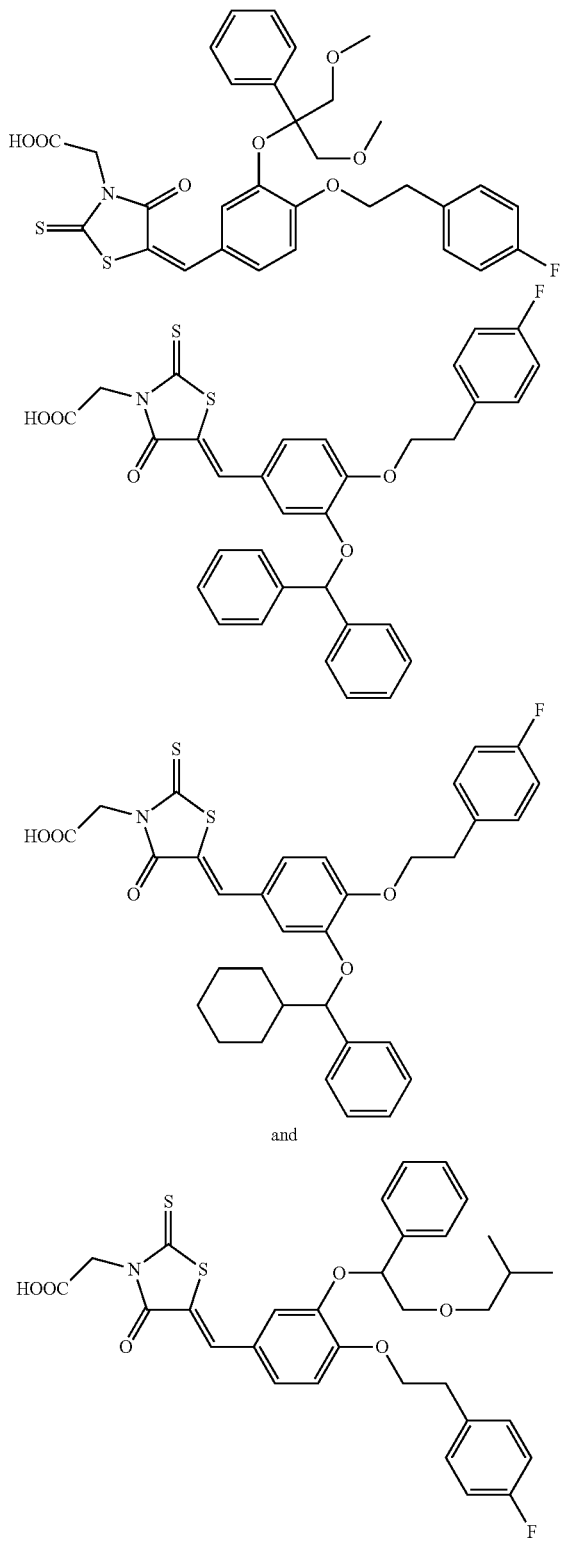

or a salt thereof.

The methods described herein are an improvement over certain prior art methods for producing proteins having reduced O-linked glycosylation in host cells in which the proteins are susceptible to O-linked glycosylation. For example, Tanner et al. in U.S. Pat. No. 5,714,377 describes a method for making recombinant proteins having reduced O-linked glycosylation using fungal cells such as yeast cells in which one or more of PMT genes encoding the Pmt protein have been genetically modified so that recombinant proteins are produced which have reduced O-linked glycosylation. While deletion of the PMT1, PMT2, or PMT4 genes in a fungal host cell enables production of a recombinant protein having reduced O-linked glycosylation in the fungal host cell, expression of the PMT genes are important for host cell growth and either deletion alone also adversely affects the ability of the fungal host cell to grow thus making it difficult to produce a sufficient quantity of host cells or recombinant protein with a reduced amount of O-linked glycosylation. Deletion of PMT2 plus either PMT1 or PMT4 appears to be lethal to the fungal host cell. Therefore, genetic elimination of the PMT genes in a host cell would appear to be an undesirable means for producing recombinant proteins having reduced O-linked glycosylation.

In contrast, the PMT genes in the host cells used in the methods of the present invention have not been modified or deleted, which enables the host cell to O-glycosylate those proteins that are important for cell growth until which time the activity of the Pmt proteins is inhibited. In general, this enables the host cells to be grown to higher levels than the levels that could be obtained if the PMT genes had been deleted. In addition, in particular embodiments, expression of the recombinant protein in the host cell is controlled by an inducible promoter and the Pmt activity in the host cell is not inhibited until expression of the recombinant protein is induced. This enables large quantities of host cells containing a nucleic acid encoding a recombinant protein to be produced in culture before inducing expression of the recombinant protein and adding the Pmt inhibitor. This can enable production of larger amounts recombinant protein having reduced O-linked glycosylation to be produced in the culture in a shorter period of time than would occur for host cells which have had one or more PMT genes deleted and grow poorly in culture.

The Pmt inhibitors described herein are improved over those described previously in Orchard et al. (U.S. Pat. No. 7,105,554) and Bobrowicz et al (U.S. Published Application No. 2007061631) based on increased potency as shown in Example 5. The increased potency allows for the use of smaller amounts of inhibitor to reduce fungal O-glycosylation to acceptable levels and/or increases the potential for complete elimination of O-glycans.

The methods described herein facilitate the production of glycoproteins having reduced O-linked glycosylation in host cells that have been genetically modified to produce glycoproteins having predominantly a particular N-linked glycan structure but which also O-glycosylate the glycoprotein. Methods for producing a wide variety of glycoproteins having predominantly particular N-linked glycoforms have been disclosed in U.S. Pat. No. 7,029,872 and U.S. Published Application Nos. 20050170452, 20050260729, 20040230042, 20050208617, 20050208617, 20040171826, 20060160179, 20060040353, and 20060211085. Any one of the host cells described in the aforementioned patent and patent applications can be used to produce a glycoprotein having predominantly a particular N-linked glycan structure and having reduced O-linked glycosylation using the method disclosed herein. It has been found that some host cells that have been genetically modified to produce glycoproteins having predominantly a particular N-linked glycan structure can grow less well in culture under particular conditions than host cells that have not been modified. For example, particular fungal and yeast cells in which genes involved in hypermannosylation have been deleted and other genes needed to produce particular mammalian or human like N-linked glycan structures have been added, can grow less well than fungal or yeast cells that do not the genetic modifications. In some of these genetically modified fungal or yeast cells, further introducing deletions of the PMT genes either is lethal to the cells or adversely affects the ability of the cells to grow to sufficient quantities in culture. The methods herein avoid the potential deleterious effects of deleting the PMT genes by allowing the cells to grow to sufficient quantities in culture before inducing expression of the recombinant glycoprotein and adding an inhibitor of the activity of the Pmt proteins, optionally with one or more a 1,2-mannosidases, to produce the recombinant glycoprotein having predominantly particular N-linked glycan structures and reduced O-linked glycosylation.

An aspect of the methods described herein is that it provides for a glycoprotein composition comprising reduced O-linked glycosylation and a predominantly a specific N-linked glycoform in which the recombinant glycoprotein may exhibit increased biological activity and/or decreased undesired immunogenicity relative to compositions of the same glycoprotein produced from mammalian cell culture, such as CHO cells. An additional advantage of producing the glycoprotein composition comprising reduced O-linked glycosylation and a predominant N-linked glycoform is that it avoids production of undesired or inactive glycoforms and heterogeneous mixtures, which may induce undesired effects and/or dilute the more effective glycoform. Thus, therapeutic pharmaceutical composition of glycoprotein molecules comprising, for example, predominantly $Man_5GlcNAc_2$, $Man_3GlcNAc_2$, $GlcNAcMan_5GlcNAc_2$, $GlcNAcMan_3GlcNAc_2$, $GlcNAc_2Man_3GlcNAc_2$, $GalGlcNAcMan_5GlcNAc_2$, $Gal(GlcNAc)_2 Man_5GlcNAc_2$, $(GalGlcNAc)_2Man_5GlcNAc_2$, $NANAGalGlcNAcMan_3GlcNAc_2$, $NANA_2Gal_2GlcNAcMan_3GlcNAc_2$, and $GalGlcNAcMan_3GlcNAc_2$ glycoforms and having reduced O-linked glycosylation may well be effective at lower doses, thus having higher efficacy/potency.

In general, the method for producing proteins having reduced O-linked glycosylation comprises transforming a host cell with a nucleic acid encoding a recombinant or heterologous protein in which it is desirable to produce the protein having reduced O-linked glycosylation. The nucleic acid encoding the recombinant protein is operably linked to regulatory sequences that allow expression of the recombinant protein. Such regulatory sequences include an inducible promoter and optionally an enhancer upstream, or 5', to the nucleic acid encoding the fusion protein and a transcription termination site 3' or down stream from the nucleic acid encoding the recombinant protein. The nucleic acid also typically encodes a 5' UTR region having a ribosome binding site and a 3' untranslated region. The nucleic acid is often a component of a vector replicable in cells in which the recombinant protein is expressed. The vector can also contain a marker to allow recognition of transformed cells. However, some cell types, particularly yeast, can be successfully transformed with a nucleic acid lacking extraneous vector sequences.

Nucleic acids encoding desired recombinant proteins can be obtained from several sources. cDNA sequences can be amplified from cell lines known to express the protein using primers to conserved regions (see, for example, Marks et al., J. Mol. Biol. 581-596 (1991)). Nucleic acids can also be synthesized de novo based on sequences in the scientific literature. Nucleic acids can also be synthesized by extension of overlapping oligonucleotides spanning a desired sequence (see, e.g., Caldas et al., Protein Engineering, 13, 353-360 (2000)).

In one aspect, the nucleic acid encoding the protein is operably linked to an inducible promoter, which allows expression of the protein to be induced when desired. In another aspect, the nucleic acid encoding the protein is operably linked to a constitutive promoter. To facilitate isolation of the expressed protein, it is currently preferable that the protein include a signal sequence that directs the protein to be excreted into the cell culture medium where it can then be isolated. In the first aspect, the transformed host cells are cultured for a time sufficient to produce a desired multiplicity of host cells sufficient to produce the desired amount of protein before adding one or more inhibitors of Pmt-mediated O-linked glycosylation to the culture medium. The inducer and inhibitor can be added to the culture simultaneously or the inducer is added to the culture before adding the one or more Pmt inhibitors or the one or more Pmt inhibitors is added to the culture before adding the inducer. The induced protein is produced having reduced O-linked glycosylation and can be recovered from the culture medium or for proteins not having a signal sequence, from the host cell by lysis. In the second aspect, wherein the nucleic acid encoding the protein is operably linked to a constitutive promoter, the one or more inhibitors of Pmt-mediated O-linked glycosylation is added to the culture medium at the same time the culture is established and the protein, which is produced having reduced O-linked glycosylation, can be recovered from the culture medium or for proteins not having a signal sequence, from the host cell by lysis.

Chemicals or compositions that inhibit the activity one or more of the Pmt proteins useful for producing proteins with reduced O-linked glycosylation are described herein. When the host cell is a lower eukaryote such as fungi or yeast, it is desirable that the inhibitor inhibit at least the activity of Pmt1 or Pmt2, or both. In higher eukaryotes, it is desirable that the inhibitor inhibit activity of the homologue in the higher eukaryote that corresponds to the Pmt1 or Pmt2.

The compounds of the invention are shown to be effective in producing recombinant proteins having reduced O-linked glycosylation in *Pichia pastoris* strains that had intact, functional PMT genes. Table 1 and FIG. 1 of Example 5 show that any one of the above four Pmt chemical inhibitors added to a culture of recombinant *Pichia pastoris* having intact, functional PMT genes and transformed with a nucleic acid encoding a recombinant, human anti-Her2 antibody protein operably linked to an inducible promoter at the time of expression of the recombinant protein was induced, produced a recombinant protein having a level of reduced O-linked glycosylation that was improved relative to the level of O-linked glycosylation seen for *Pichia pastoris* cells treated with Pmt inhibitor Pmti-3 described in Orchard et al. (Bioorgan & Med Chem Letters (2004) 14:3975-3978) and patent publications by the same authors including EP 1313471 B1 and Bobrowicz et al. U.S. Published Application No. 2007061631.

Host Cells

The term "cells" as used herein refers to host cells described as follows. While host cells for the method herein includes both higher eukaryote cells and lower eukaryote cells, lower eukaryote cells, for example filamentous fungi or yeast cells, are currently preferred for expression of proteins because they can be economically cultured, give high yields of protein, and when appropriately modified are capable of producing proteins having suitable glycosylation patterns. Lower eukaryotes include yeast, fungi, collar-flagellates, microsporidia, alveolates (e.g., dinoflagellates), stramenopiles (e.g., brown algae, protozoa), rhodophyta (e.g., red algae), plants (e.g., green algae, plant cells, moss) and other protists. Yeast and fungi include, but are not limited to: *Pichia* sp. (for example, *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica*), *Saccharomyces* sp. (for example *Saccharomyces cerevisiea*), *Hansenula polymorpha, Kluyveromyces* sp. (for example, *Kluyveromyces lactis*), *Candida albicans, Aspergillus* sp (for example, *Aspergillus nidulans, Aspergillus niger, Aspergillus oryzae*), *Trichoderma reesei, Chrysosporium lucknowense, Fusarium* sp. (for example, *Fusarium gramineum, Fusarium venenatum*), *Physcomitrella patens* and *Neurospora crassa*. Yeast, in particular, are currently preferred because yeast offers established genetics allowing for rapid transformations, tested protein localization strategies, and facile gene knock-out techniques. Suitable vectors have expression control sequences, such as promoters, including 3-phosphoglycerate kinase or other glycolytic enzymes, and an origin of replication, termination sequences, and the like as desired.

Various yeasts, such as *K. lactis, Pichia pastoris, Pichia methanolica*, and *Hansenula polymorpha* are currently preferred for cell culture because they are able to grow to high cell densities and secrete large quantities of recombinant protein. Likewise, filamentous fungi, such as *Aspergillus niger, Fusarium* sp, *Neurospora* crass, and others can be used to produce recombinant proteins at an industrial scale.

Lower eukaryotes, in particular filamentous fungi and yeast, can be genetically modified so that they express proteins or glycoproteins in which the glycosylation pattern is human-like or humanized. This can be achieved by eliminating selected endogenous glycosylation enzymes and/or supplying exogenous enzymes as described by Gerngross et al. in U.S. Pat. No. 7,029,872, and U.S. Published Patent Application Nos. 20040018590, 20050170452, 20050260729, 20040230042, 20050208617, 20040171826, 20050208617, 20060160179, 20060040353, and 20060211085. Thus, a host cell can additionally or alternatively be engineered to express one or more enzymes or enzyme activities, which enable the production of particular N-glycan structures at a high yield. Such an enzyme can be targeted to a host subcellular organelle in which the enzyme will have optimal activity, for example, by means of signal peptide not normally associated with the enzyme. Host cells can also be modified to express a sugar nucleotide transporter and/or a nucleotide diphosphatase enzyme. The transporter and diphosphatase improve the efficiency of engineered glycosylation steps, by providing the appropriate substrates for the glycosylation enzymes in the appropriate compartments, reducing competitive product inhibition, and promoting the removal of nucleoside diphosphates. See, for example, Gerngross et al. in U.S. Published Patent Application No. 20040018590 and Hamilton, 2003, Science 301: 1244-46 and the aforementioned U.S. patent and patent applications.

By way of example, a host cell (for example, yeast or fungal) can be selected or engineered to be depleted in 1,6-mannosyl transferase activities, which would otherwise add mannose residues onto the N-glycan of a glycoprotein, and to further include a nucleic acid for ectopic expression of an α-1,2 mannosidase activity, which enables production of recombinant glycoproteins having greater than 30 mole percent $Man_5GlcNAc_2$ N-glycans. When a glycoprotein is produced in the host cells according to the method described herein, the host cells will produce a glycoprotein having predominantly a $Man_5GlcNAc_2$ N-glycan structure and reduced O-glycosylation compared to the glycoprotein produced in the cell otherwise. In a further aspect, the host cell is engineered to further include a nucleic acid for ectopic expression of GlcNAc transferase I activity, which enables production of glycoproteins having predominantly $GlcNAcMan_5GlcNAc_2$ N-glycans. When a glycoprotein is produced in the host cells according to the method described herein, the host cells will produce a glycoprotein having predominantly a $GlcNAcMan_5GlcNAc_2$ N-glycan structure and reduced O-glycosylation compared to the glycoprotein produced in the cell otherwise. In a further still aspect, the host cell is engineered to further include a nucleic acid for ectopic expression of mannosidase II activity, which enables production of glycoproteins having predominantly $GlcNAcMan_3GlcNAc_2$ N-glycans. When a glycoprotein is produced in the host cells according to the method described herein, the host cells will produce a glycoprotein having predominantly a $GlcNAcMan_3GlcNAc_2$ N-glycan structure and reduced O-glycosylation compared to the glycoprotein produced in the cell otherwise. In a further still aspect, the host cell is engineered to further include a nucleic acid for ectopic expression of GlcNAc transferase II activity, which enables production of glycoproteins having predominantly $GlcNAc_2Man_3GlcNAc_2$ N-glycans. When a glycoprotein is produced in the host cells according to the method described herein, the host cells will produce a glycoprotein having predominantly a $GlcNAc_2Man_3GlcNAc_2$ N-glycan structure and reduced O-glycosylation compared to the glycoprotein produced in the cell otherwise. In further still aspects, the above host cells can be further engineered to produce particular hybrid or complex N-glycan or human-like N-glycan structures by further including one or more higher eukaryote genes involved in N-linked glycosylation, in any combination, that encode for example, sialytransferase activities, class II and III mannosidase activities, GlcNAc transferase II, III, IV, V, VI, IX activity, and galactose transferase activity. It is currently preferable that the cells further include one or more of nucleic acids encoding UDP-specific diphosphatase activity, GDP-specific diphosphatase activity, and UDP-GlcNAc transporter activity.

Plants and plant cell cultures may be used for expression of proteins and glycoproteins with reduced O-linked glycosylation as taught herein (See, for example, Larrick & Fry, 1991, Hum. Antibodies Hybridomas 2: 172-89); Benvenuto et al., 1991, Plant Mol. Biol. 17: 865-74); Durin et al., 1990, Plant Mol. Biol. 15: 281-93); Hiatt et al., 1989, Nature 342: 76-8). Preferable plant hosts include, for example, *Arabidopsis, Nicotiana tabacum, Nicotiana rustica*, and *Solanum tuberosum*.

Insect cell culture can also be used to produce proteins and glycoproteins proteins and glycoproteins with reduced O-linked glycosylation, as taught herein for example, baculovirus-based expression systems (See, for example, Putlitz et al., 1990, Bio/Technology 8: 651-654).

Although not currently as economical to culture as lower eukaryotes and prokaryotes, mammalian tissue cell culture can also be used to express and produce proteins and glycoproteins with reduced O-linked glycosylation as taught herein (See Winnacker, From Genes to Clones (VCH Publishers, NY, 1987). Suitable hosts include CHO cell lines, various COS cell lines, HeLa cells, preferably myeloma cell lines or the like or transformed B-cells or hybridomas. Expression vectors for these cells can include expression control sequences, such as an origin of replication, a promoter, an enhancer (Queen et al., 19861, mmunol. Rev. 89:49-68), and necessary processing information sites, such as ribosome binding sites, RNA splice sites, polyadenylation sites, and transcriptional terminator sequences. Expression control sequences are promoters derived from immunoglobulin genes, SV40, Adenovirus, bovine Papilloma Virus, cytomegalovirus and the like. Generally, a selectable marker, such as a neoR expression cassette, is included in the expression vector.

The nucleic acid encoding the protein to be expressed can be transferred into the host cell by conventional methods, which vary depending on the type of cellular host. For example, calcium phosphate treatment, protoplast fusion, natural breeding, lipofection, biolistics, viral-based transduction, or electroporation can be used for cellular hosts. Tungsten particle ballistic transgenesis is preferred for plant cells and tissues. (See, generally, Maniatis et al., Molecular Cloning: A Laboratory Manual (Cold Spring Harbor Press, 1982))

Once expressed, the proteins or glycoproteins having reduced O-linked glycosylation can be purified according to standard procedures of the art, including ammonium sulfate precipitation, affinity columns, column chromatography, gel electrophoresis and the like (See, generally, Scopes, R., Protein Purification (Springer-Verlag, N.Y., 1982)). Substantially pure glycoproteins of at least about 90 to 95% homogeneity are preferred, and 98 to 99% or more homogeneity most preferred, for pharmaceutical uses. Once purified, partially or to homogeneity as desired, the proteins can then be used therapeutically (including extracorporeally) or in developing and performing assay procedures, immunofluorescent stainings, and the like. (See, generally, Immunological Methods, Vols. I and II (Lefkovits and Pernis, eds., Academic Press, NY, 1979 and 1981).

Therefore, further provided are glycoprotein compositions comprising a predominant species of N-glycan structure and having reduced O-linked glycosylation compared to compositions of the glycoprotein which have been produced in host cells have not been incubated in the presence of an inhibitor of Pmt-mediated O-linked glycosylation or an α-1,2-mannosidase capable of trimming more than one mannose residue from a glycans structure or both. In particular aspects, the glycoprotein composition comprises a glycoprotein having a predominant N-glycan structure selected from the group consisting of $Man_5GlcNAc_2$, $Man_3GlcNAc_2$, $GlcNAcMan_5GlcNAc_2$, $GlcNAcMan_3GlcNAc_2$, $GlcNAc_2Man_3GlcNAc_2$, $GalGlcNAcMan_5GlcNAc_2$, $Gal(GlcNAc)_2Man_5GlcNAc_2$, $(GalGlcNAc)_2Man_5GlcNAc_2$, $NANAGalGlcNAcMan_3GlcNAc_2$, $NANA_2Gal_2GlcNAcMan_3GlcNAc_2$, and $GalGlcNAcMan_3GlcNAc_2$ glycoforms.

Pharmaceutical Compositions

Proteins and glycoproteins having reduced O-linked glycosylation can be incorporated into pharmaceutical compositions comprising the glycoprotein as an active therapeutic agent and a variety of other pharmaceutically acceptable components (See, Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation can also include other carriers, adjuvants, or nontoxic, nontherapeutic, nonimmunogenic stabilizers, and the like.

Pharmaceutical compositions for parenteral administration are sterile, substantially isotonic, pyrogen-free and prepared in accordance with GMP of the FDA or similar body. Glycoproteins can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Glycoproteins can be administered in the form of a depot injection or implant preparation which can be formulated in such a manner as permit a sustained release of the active ingredient. Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (See Langer, Science 249, 1527 (1990) and Hanes, Advanced Drug Delivery Reviews 28, 97-119 (1997).

The term "or a salt thereof" refers to salts prepared from acceptable bases including inorganic or organic bases. Salts derived from inorganic bases include aluminum, ammonium, calcium, copper, ferric, ferrous, lithium, magnesium, manganic salts, manganous, potassium, sodium, zinc, and the like. Salts in the solid form may exist in more than one crystal structure, and may also be in the form of hydrates. Salts derived from bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention may contain one or more asymmetric centers and can thus occur as racemates and racemic mixtures, single enantiomers, diastereomeric mixtures and individual diastereomers. The present invention is meant to comprehend all such isomeric forms of these compounds.

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, for example, Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999).

The following examples provide methods for preparing various Pmt inhibitors of the invention.

EXAMPLE 1

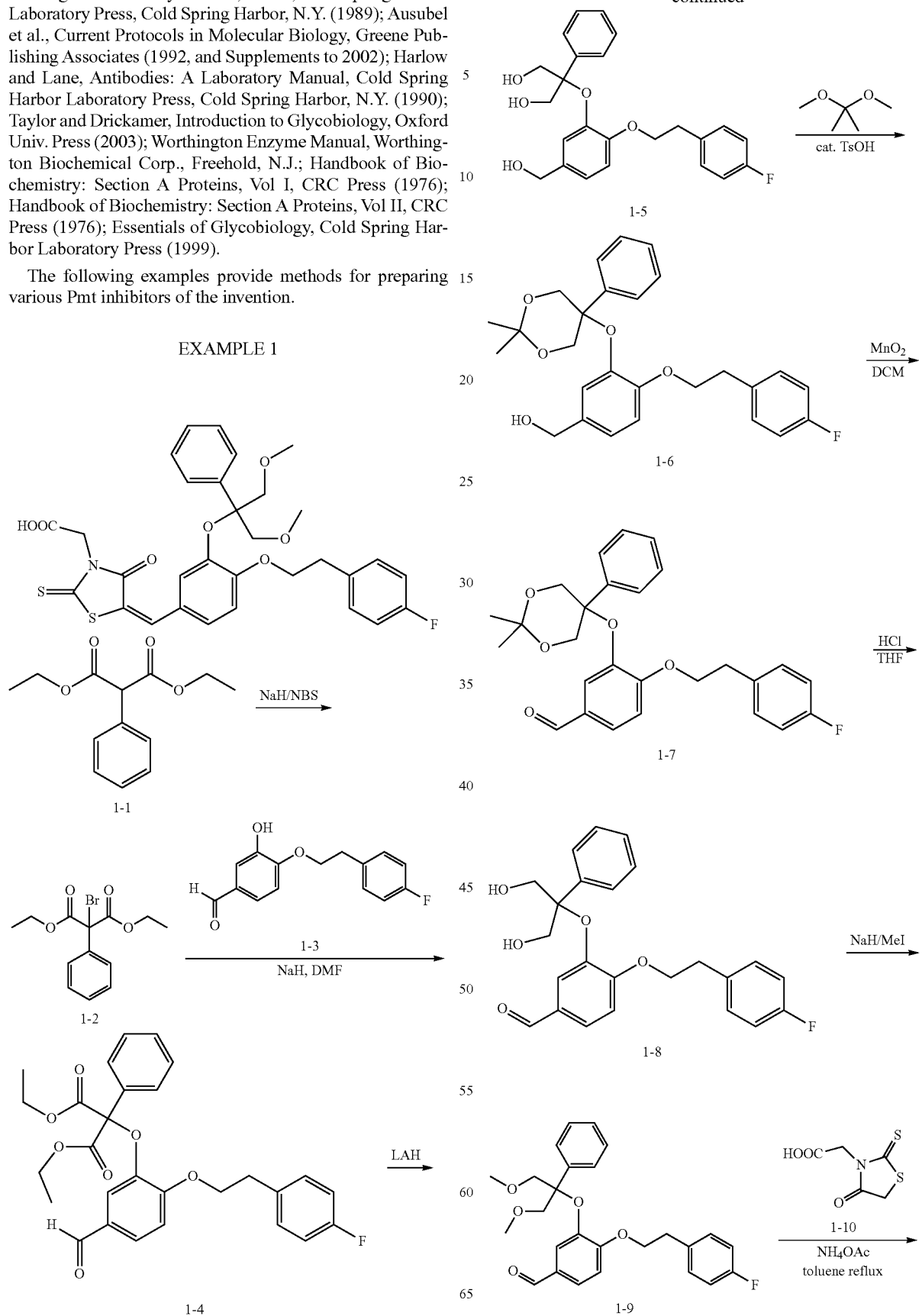

EXAMPLE 1

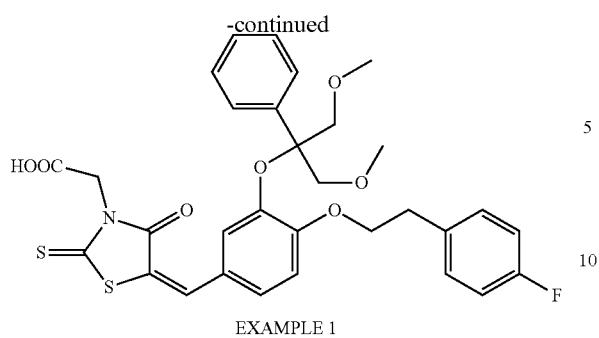

EXAMPLE 1

Step A

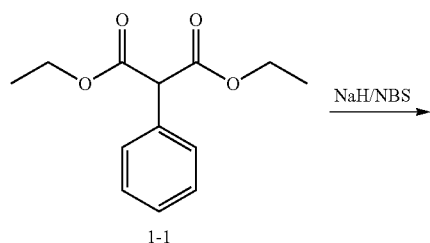

1-1

→ NaH/NBS

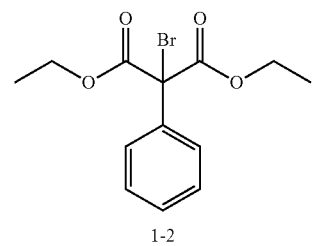

1-2

To a solution of 1-1 (5.90 g, 25 mmol) in THF (200 mL) was added NaH (2.0 g, 50 mmole) portionwise. The resulting mixture was stirred at 0° C. for half an hour. Then NBS (4.86 g, 27.5 mmol) was added into and stirred for 15 minutes. The white solid was filtered and the filtration was concentrated to give a residue, which was dissolved in $CHCl_3$ and dried over $Na_2SO_4$. The solvent was evaporated to give 1-2 (5 g, yield 63%), which was used for next step without further purification.

Step B

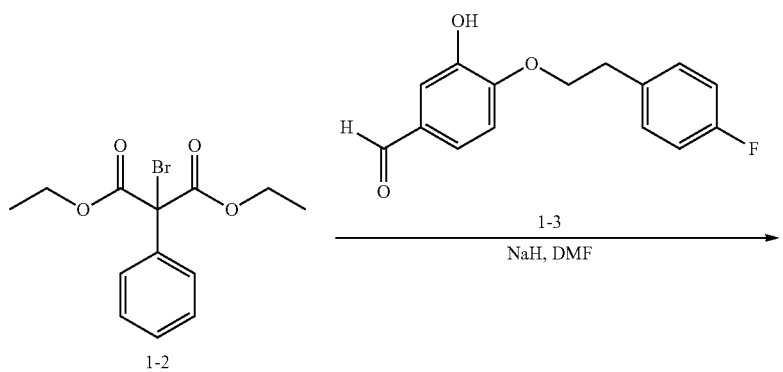

1-2     1-3
→ NaH, DMF

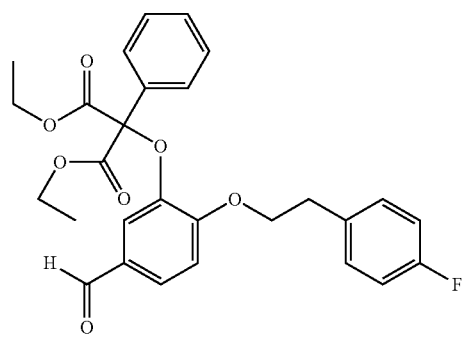

1-4

To a solution of 1-2 (1.8 g, 6 mmol) and 1-3 (1.3 g, 5 mmol) in dried DMF (5 mL) was added NaH (2.4 g g, 10 mmol) and then stirred at room temperature overnight. The resulting mixture was partitioned between water and EtOA. The combined organic layer were washed with brine, dried over sodium sulfate and concentrated. The residue was purified by prep-TLC to give 1-4 (800 mg, yield 40%). $^1$H-NMR (400 MHz, CDCl$_3$) δ 9.66 (s, 1H), 7.74~7.71 (m, 2H), 7.49~1.46 (m, 1H), 7.37~7.33 (m, 5H), 7.20 (d, J=2.02 Hz, 1H), 6.97~6.92 (m, 3H), 4.28~4.19 (m, 6H), 3.16 (t, J=6.6 Hz, 2H), 1.11 (m, 6H).

Step C

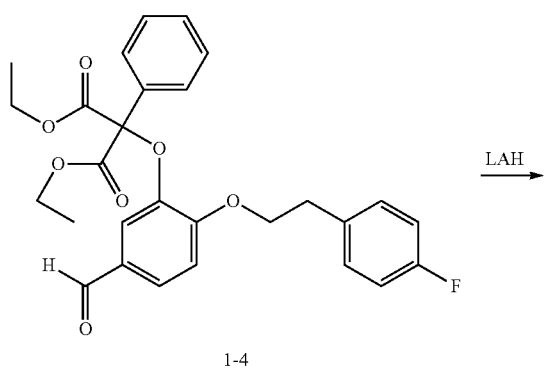

1-4

To a suspension of LAH (380 mg, 10 mmol) in THF (50 mL) was added 1-4 (1.3 g, 2.6 mmol) at 0° C. and the resulting mixture was stirred at room temperature for 30 min. The mixture was carefully treated by diluted aq. HCl and then partitioned between water and EtOAc. The organic layer was washed by brine, dried over sodium sulfate and concentrated. The residue was purified by prep-TLC to give 1-5 (260 mg, 20% yield).

Step D

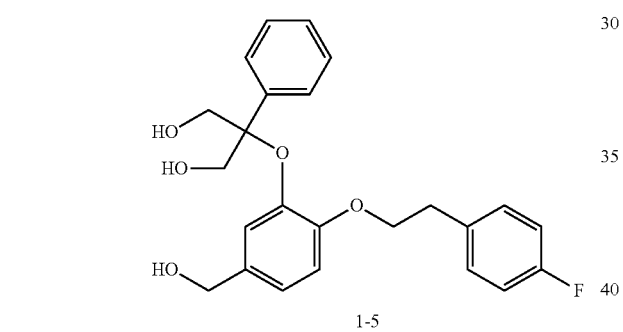

1-5

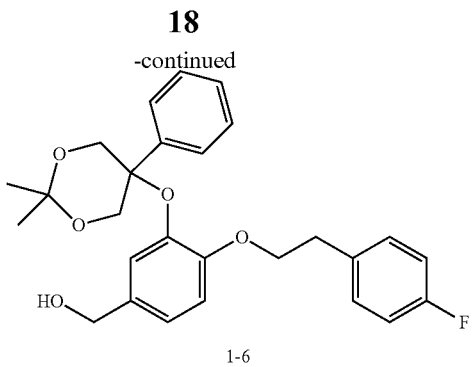

1-6

To a solution of 1-5 (300 mg, 0.54 mmol) in 2,2-dimethoxylpropane (1 mL) was added catalytic amount TsOH.H$_2$O (~10 mg) and then the resulting mixture was stirred for one hour at room temperature. The mixture was purified directly by prep-TLC to give 1-6 (100 mg, yield 28%). $^1$H-NMR (400 MHz, MeOD) δ ppm 7.52 (d, J=8.05 Hz, 2H), 7.40~7.15 (m, 5H), 6.90~6.85 (m, 2H), 6.80~6.75 (m, 2H), 4.25 (s, 2H), 4.23 (m, 6H), 3.0 (m, 2H), 1.48 (t, 6H).

Step E

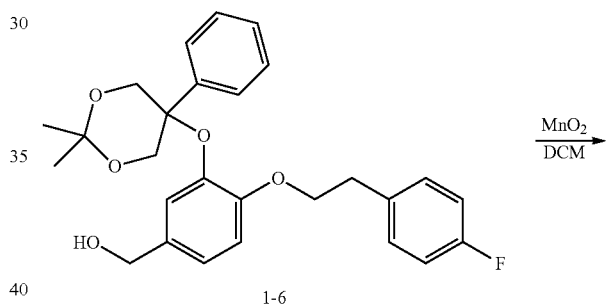

1-6

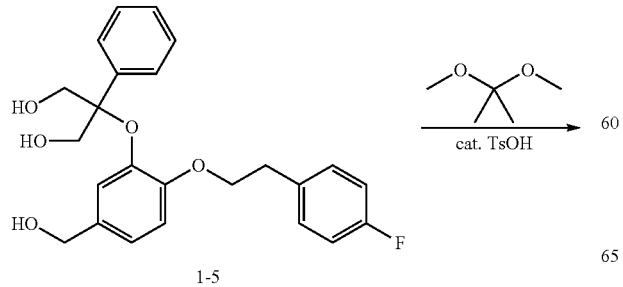

1-7

To a solution of 1-6 (100 mg, 0.22 mmol) in dried DCM (25 mL) was added MnO$_2$ (174 mg, 2 mmol) in one portion and the resulting mixture was heated to reflux for about 2 hrs. After cooling to room temperature, the mixture was filtered and the filtration was concentrated and the residue was purified by prep-TLC to give 1-7 (60 mg, yield 60%). $^1$H-NMR (400 MHz, MeOD) δ ppm 9.5 (s, 1H), 7.52 (d, J=7.2 Hz, 1H), 7.48 (d, J=2.8 Hz, 2H), 7.30 (m, 3H), 7.25 (m, 6H), 7.0 (t, J=8.6 Hz, 2H), 6.89 (m, J=8.6 Hz, 2H), 6.76 (d, J=8 Hz, 1H), 4.23 (m, 6H), 3.0 (m, 2H), 1.48 (t, 6H).

Step F

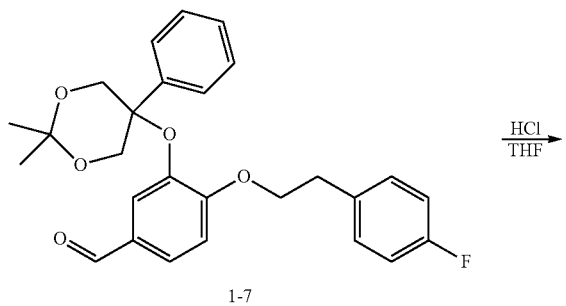

1-7

To a solution of 1-7 (80 mg, 0.17 mmol) in THF was added 6 N HCl and the resulting mixture was stirred at room temperature for 2 hours. The solvent was removed in vacuo to afford the crude 1-8 (60 mg, 82% yield), which was subjected to next step without further purification.

Step G

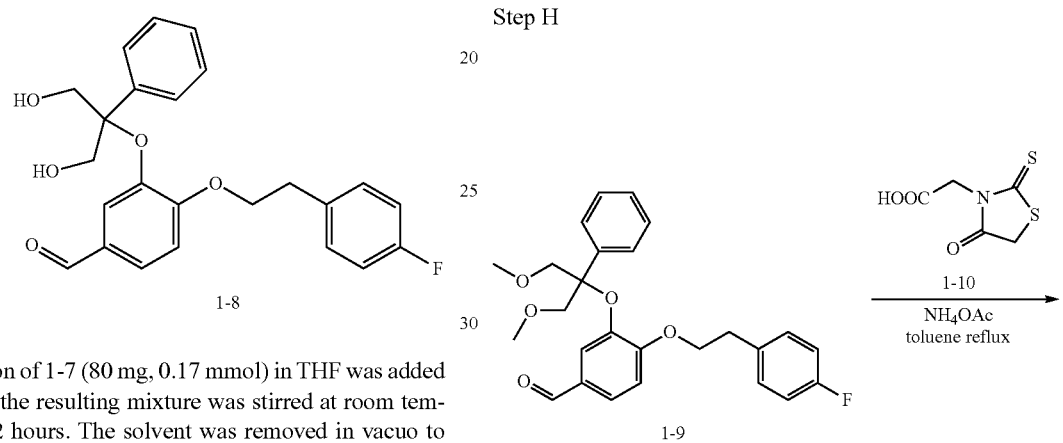

To a solution of 1-8 (60 mg, 0.146 mmol) in DMF (6 mL) was added NaH (24 mg, 1 mmol) at 0° C. and the resulting mixture was stirred at the same temperature for about 30 min and then CH$_3$I (0.2 mL) was added into. The mixture was stirred at the same temperature for another one hour. The mixture was then partitioned between H$_2$O and EtOAc. The combined organic layers were washed with brine, dried over sodium sulfate, and concentrated. The residue was purified by prep-TLC to give 1-9 (40 mg, yield 63.0%). $^1$H-NMR (400 MHz, MeOD) S ppm 9.6 (s, 1H), 7.52 (d, J=8.08 Hz, 2H), 7.43 (m, 1H), 7.36-7.30 (m, 5H), 7.16 (d, J=2.02 Hz, 1H), 7.0 (t, J=8.6 Hz, 2H), 6.89 (m, J=8.6 Hz, 2H), 4.23 (t, J=6.56 Hz, 2H), 3.95-3.85 (m, 4H), 3.30 (s, 6H), 3.13 (dd, J$_1$=6.26 Hz, J$_2$=6.26 Hz, 2H).

Step H

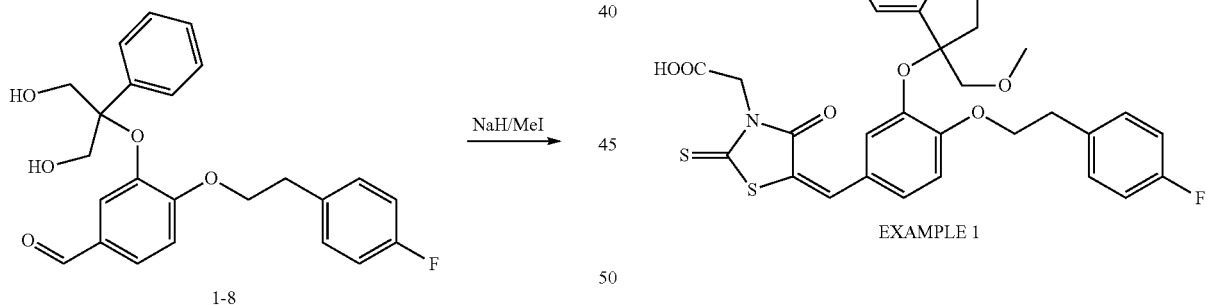

EXAMPLE 1

A mixture of 1-9 (40 mg, 0.09 mmol), 1-10 (19 mg, 0.09 mmol) and NH$_4$OAc (70 mg, 0.9 mmol) in toluene (10 mL) was heated under nitrogen to reflux for about 3 hrs. After cooling to room temperature, the resulting mixture was treated by diluted aq. HCl until pH=4~5 and then partitioned between H$_2$O and EtOAc. The combined organic layers were washed by brine, dried over Na$_2$SO$_4$ and concentrated. The residue was purified by prep-HPLC to give EXAMPLE 1 (30 mg, yield 50%) as a yellow solid. $^1$H-NMR (400 MHz, MeOD) δ ppm 7.46~7.53 (m, 3H), 7.31~7.40 (m, 5H), 7.15~7.18 (m, 1H), 6.92~7.06 (m, 4H), 4.71 (s, 2H), 4.25~4.30 (m, 2H), 3.85~3.94 (m, 4H), 3.26~3.29 (m, 6H), 3.10~3.13 (dd, J=6.26 Hz, J=6.26 Hz, 2H). MS m/z 612(M+1)$^+$.

EXAMPLE 2

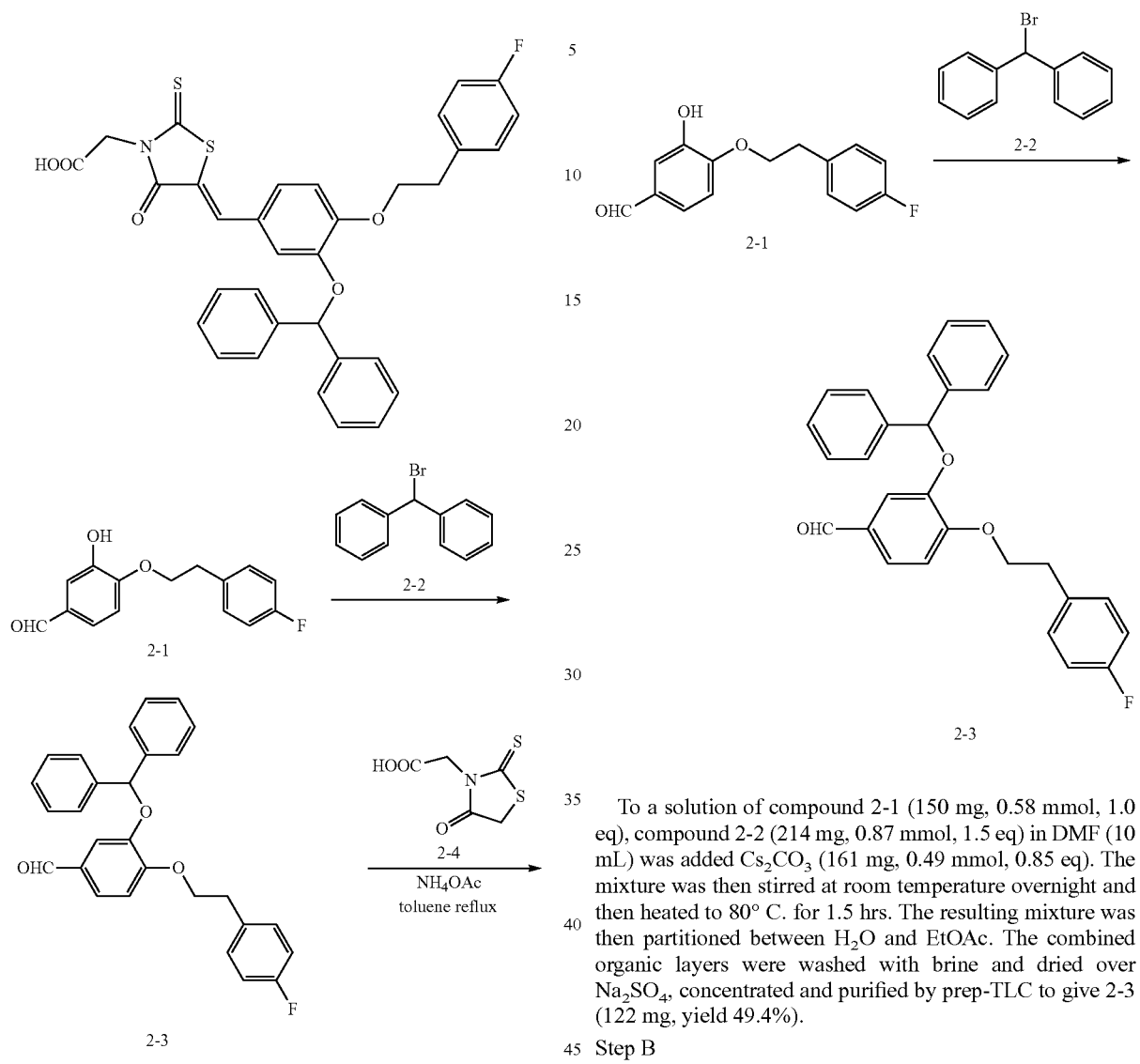

Step A

To a solution of compound 2-1 (150 mg, 0.58 mmol, 1.0 eq), compound 2-2 (214 mg, 0.87 mmol, 1.5 eq) in DMF (10 mL) was added Cs$_2$CO$_3$ (161 mg, 0.49 mmol, 0.85 eq). The mixture was then stirred at room temperature overnight and then heated to 80° C. for 1.5 hrs. The resulting mixture was then partitioned between H$_2$O and EtOAc. The combined organic layers were washed with brine and dried over Na$_2$SO$_4$, concentrated and purified by prep-TLC to give 2-3 (122 mg, yield 49.4%).

Step B

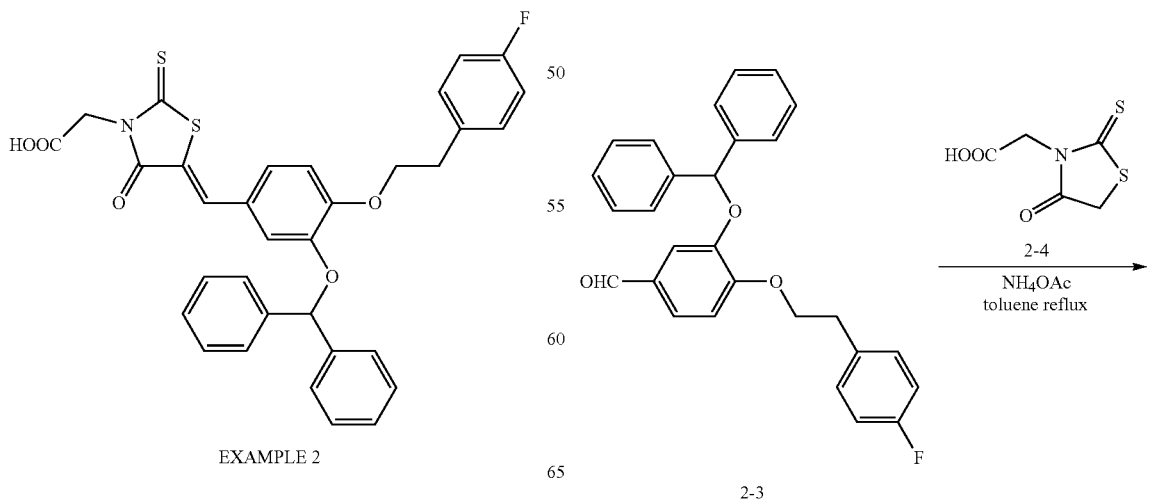

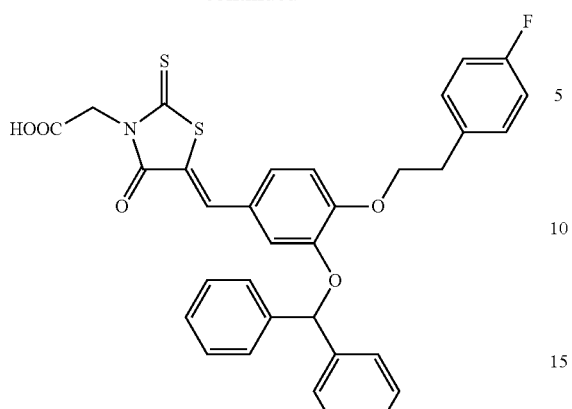

EXAMPLE 2

A mixture of compound 2-3 (122 mg, 0.29 mmol, 1.0 eq), 2-4 (57 mg, 0.30 mmol, 1.05 eq) and NH$_4$OAc (223 mg, 2.90 mmol, 10.0 eq) in toluene (15 mL) was heated under nitrogen to reflux for about 3 h. The resulting mixture was treated by 10% HCl acid to pH=4-5, and then partitioned between H$_2$O and EtOAc. The combined organic layers were washed with brine and dried over Na$_2$SO$_4$, concentrated and purified by prep-TLC to give EXAMPLE 2 (52 mg, yield 29.9%). $^1$H-NMR (400 MHz, MeOD) δ 7.41-7.47 (m, 3H), 7.19-7.35 (m, 10H), 6.99-7.07 (m, 3H), 6.87-6.92 (m, 2H), 6.22 (s, 1H), 4.75 (s, 2H), 4.24-4.29 (m, 2H), 3.72-3.13 (m, 2H). MS m/z 600 (M+1)$^+$

EXAMPLE 3

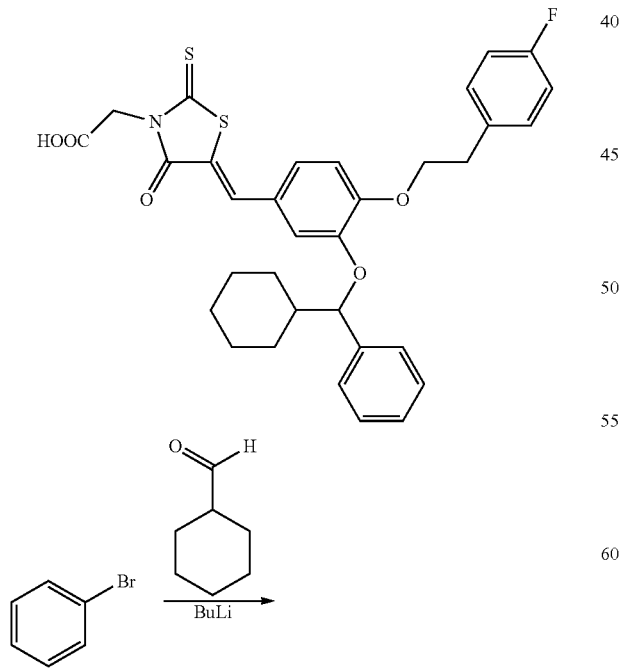

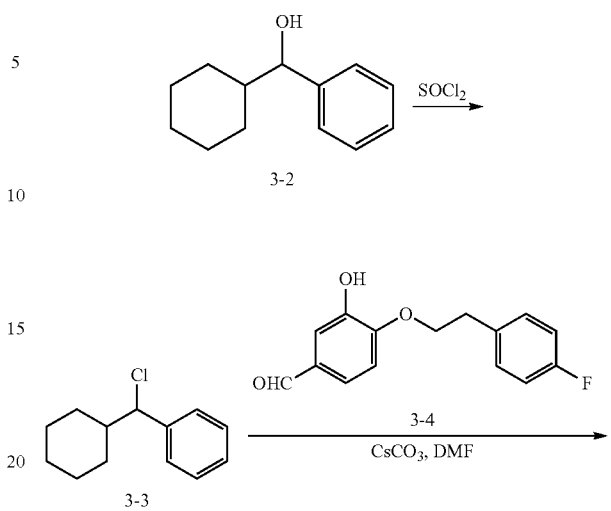

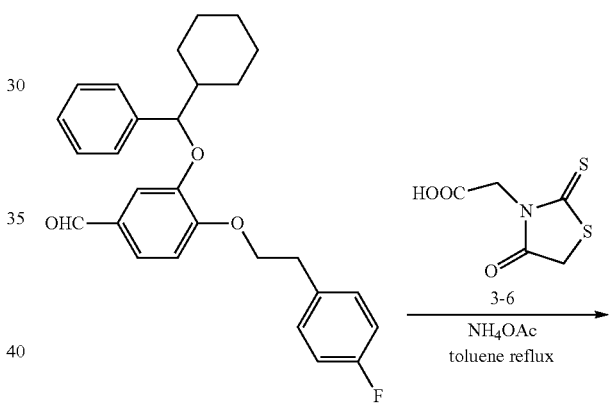

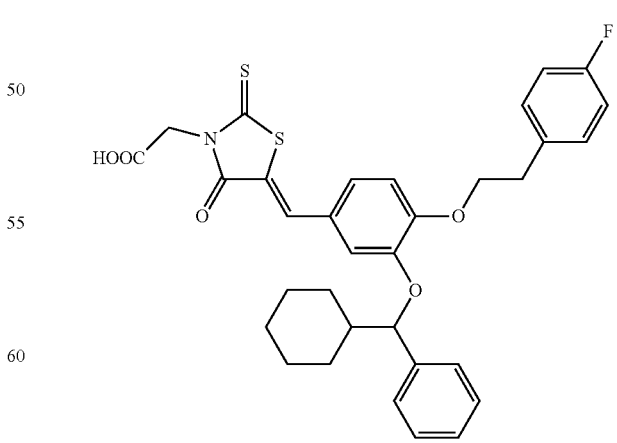

EXAMPLE 3

Step A

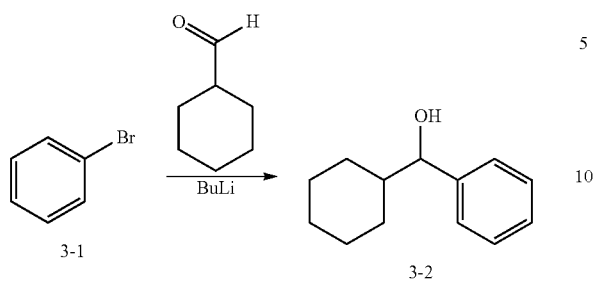

To a solution of 3-1 (1 g, 6.37 mmol) in dry THF (20 mL) was added BuLi (3 mL, 7.68 mmol) dropwise at −70° C. and then the mixture was stirred for 30 min at room temperature. After cooling to −70° C. again, a solution of cyclohexanecarbaldehyde (0.72 g, 6.43 mmol) in dry THF (5 mL) was added dropwise. After stirring for 30 min, saturated aqueous NH$_4$Cl was added into the mixture and the resulting mixture was extracted with EtOAc. The organic layers were combined and dried over Na$_2$SO$_4$, concentrated to give 3-2 (1.52 g, 14.3%) as a crude oil.

Step B

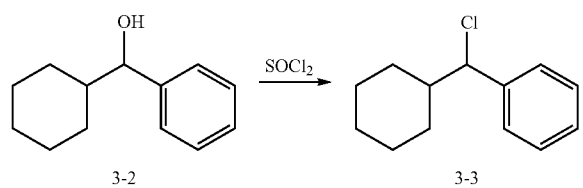

To the mixture of 3-2 (600 mg, 3.1 mmol) in dry DCM (15 mL) was added SOCl$_2$ (2 mL) dropwise at 0° C. Then the resulting mixture was stirred for 2 h at room temperature. The mixture was concentrated under reduced pressure and then diluted with EtOAc. The organic layer was washed with saturated aqueous NaHCO$_3$, brine, dried over Na$_2$SO$_4$, and then concentrated to give 3-3 (500 mg, crude).

Step C

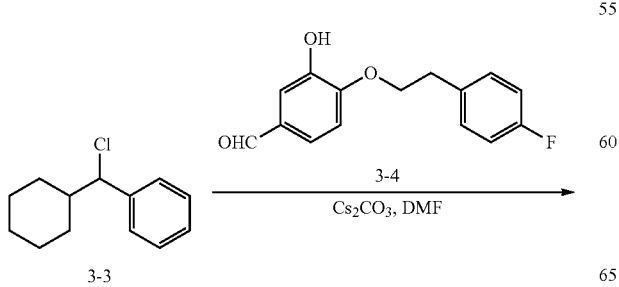

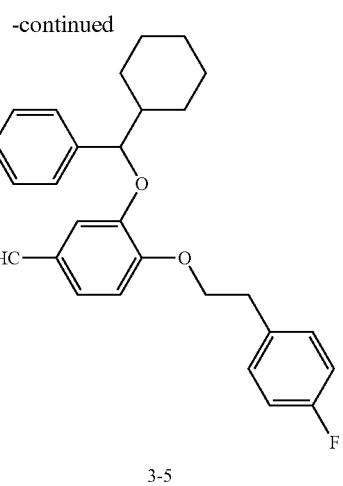

To a solution of 3-3 (450 mg, crude) and 3-4 (375 mg, 1.44 mmol) in DMF (10 mL) was added Cs$_2$CO$_3$ (399 mg, 1.22 mmol) in one portion and then the mixture was heated to 110° C. for 18 h. The mixture was diluted with H$_2$O and extracted with EtOAc. The organic layers were combined and dried over Na$_2$SO$_4$, concentrated. The residue was purified by TLC to afford 3-5 (130 mg) as oil, which was used for next step directly.

Step D

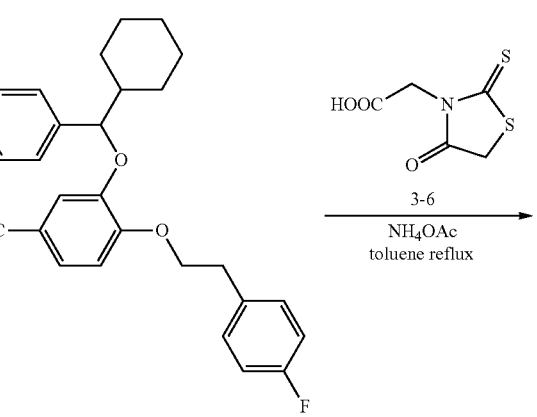

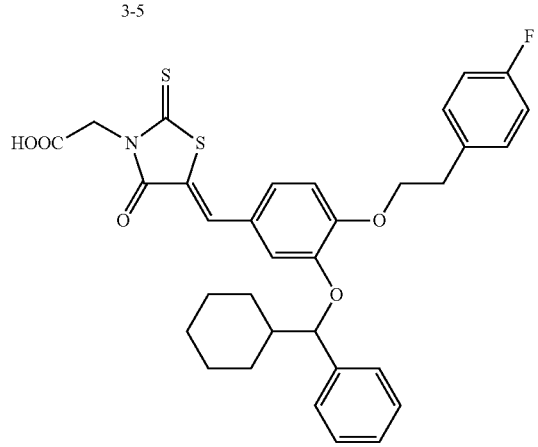

EXAMPLE 3

To a mixture of 3-5 (130 mg, 0.3 mmol) and 3-6 (60 mg, 0.31 mmol) in toluene (15 mL) was added NH₄OAc (180 mg, 2.34 mmol) in one portion and then the mixture was heated to reflux for 3.5 h. Then the mixture was cooled to room temperature and aqueous 10% HCl was added to pH=5. The mixture was extracted with EtOAc. The organic layers were combined and dried over Na₂SO₄, concentrated to give yellow oil. The residue was purified by prep-TLC to afford EXAMPLE 3 (150 mg, yield 82.4%). ¹H-NMR (300 MHz, MeOD) δ 7.60 (s, 1H), 7.19-7.49 (m, 11H), 6.88 (s, 1H), 6.81 (s, 1H), 5.05 (s, 1H), 4.65 (s, 2H), 4.25~4.39 (m, 2H), 3.15 (m, 2H), 1.60~4.98 (m, 5H), 1.00~4.46 (m, 6H). MS m/z: 607 (M+1)⁺.

EXAMPLE 4

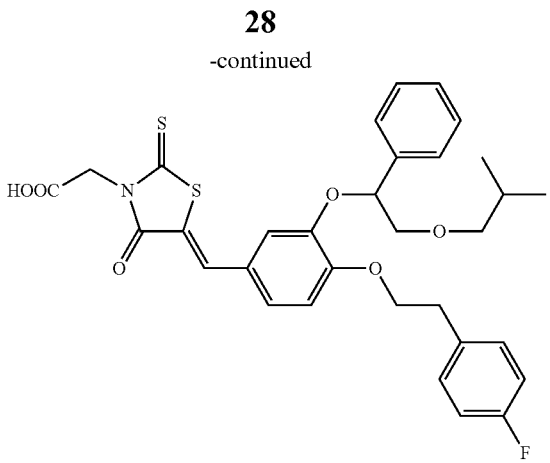

EXAMPLE 4

Step A

Sodium (8.5 mg, 0.37 mmol) was dissolved at 40° C. in 2-methyl-propan-1-ol (1.3 g, 17.5 mmol) and compound 4-1 (2 g, 16.7 mmol) were subsequently added dropwise at 50° C. over 30 min. Then the reaction mixture was heated to 70° C. and stirred overnight. The resulting mixture was partitioned between H₂O and EtOAc. The organic layer was washed with brine, dried over sodium sulfate and concentrated to give 4-2 (1.0 g, crude), which is used for the next step directly.

Step B

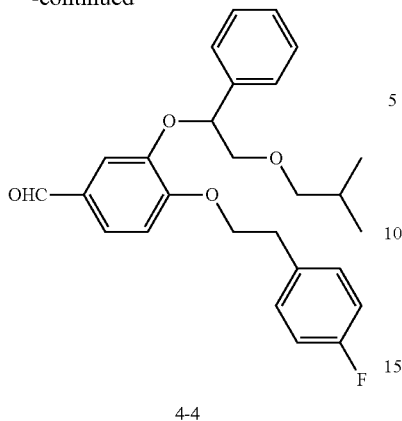

4-4

To a solution of 4-2 (1.0 g, crude), 4-3 (400 mg, 1.64 mmol, 1.0 eq) and PPh$_3$ (516 mg, 1.96 mmol, 1.2 eq) in THF (20 mL) was added DIAD (406 mg, 1.96 mmol, 1.2 eq) dropwise at 0° C. The resulting mixture was stirred at room temperature overnight and then partitioned between H$_2$O and EtOAc. The organic layer was washed by brine, dried over Na$_2$SO$_4$, concentrated and purified by prep-HPLC to give 4 (90 mg, yield 12.0%). $^1$H-NMR (400 MHz, MeOD) δ 9.72 (s, 1H), 7.28-7.40 (m, 9H), 6.98-7.05 (t, J=8.78 Hz, 2H), 6.89-6.92 (d, J=8.28 Hz, 1H), 5.42-5.46 (m, 1H), 4.22-4.32 (m, 2H), 3.86-3.92 (m, 1H), 3.68-3.74 (m, 1H), 3.24-3.34 (m, 2H), 3.12-3.18 (m, 2H), 1.82-1.90 (m, 1H), 0.84-0.88 (m, 6H).

Step C

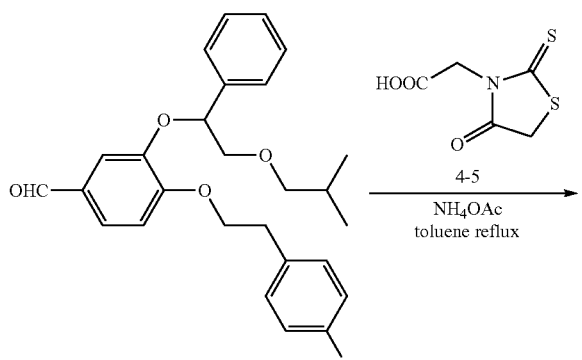

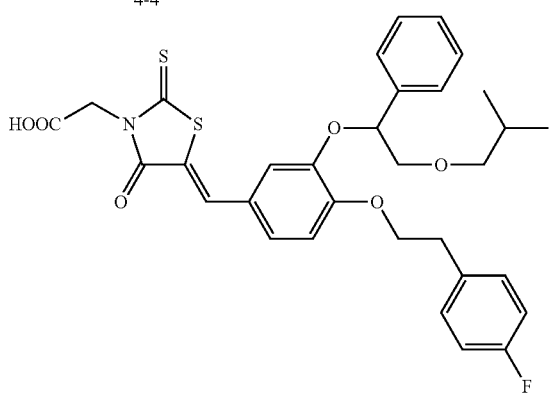

EXAMPLE 4

The preparation of EXAMPLE 4 is the same as that for EXAMPLE 3. $^1$H-NMR (400 MHz, MeOD) δ 7.49 (s, 1H), 7.24-7.40 (m, 7H), 6.98-7.05 (m, 4H), 6.90-6.91 (m, 1H), 5.37-5.40 (m, 1H), 4.75 (s, 2H), 4.21-4.32 (m, 2H), 3.83-3.88 (m, 1H), 3.69-3.72 (m, 1H), 3.33-3.35 (m, 2H), 3.09-3.13 (t, J=6.57 Hz, 2H), 1.79-1.87 (m, 1H), 0.86-0.88 (m, 6H).

EXAMPLE 5

This example shows that *Pichia pastoris* transformed with an expression vector encoding the heavy chain (Hc) and light chain (Lc) of the human anti-Her2 antibody and treated with the novel Pmt inhibitors described herein produced a glycoprotein having reduced O-glycosylation.

Expression/integration plasmid vector pGLY2988 contains expression cassettes under control of the methanol-inducible *Pichia pastoris* AOX1 promoter that encode the heavy (Hc) and light (Lc) chains of anti-Her2. Anti-Her2 Hc and Lc fused at the N-terminus to α-MAT pre signal peptide (SEQ ID Nos:1 and 2) were synthesized by GeneArt AG. Each was synthesized with unique 5' EcoR1 and 3' Fse1 sites. The nucleotide and amino acid sequences of the anti-Her2 Hc are shown in SEQ ID Nos:3 and 4, respectively. The nucleotide and amino acid sequences of the anti-Her2 Lc are shown in SEQ ID Nos:5 and 6, respectively. Both nucleic acid fragments encoding the Hc and Lc proteins fused to the α-MAT pre signal peptide were separately subcloned using 5' EcoR1 and 3' Fse1 unique sites into an expression plasmid vector pGLY2198, which contains the *Pichia pastoris* TRP2 targeting nucleic acid and the Zeocin-resistance marker and generates expression cassettes under the control of the AOX1 promoter and *Saccharomyces cerevisiae* CYC terminator, to form plasmid vectors pGLY2987 and pGLY2338, respectively. The Lc expression cassette was then removed from plasmid vector pGLY2338 by digesting with BamHI and NotI and subcloned into plasmid vector pGLY2987 digested with BamH1 and Not1, thus generating the final expression plasmid vector pGLY2988.

Anti-Her2 expression strain yGLY4280 was constructed as follows: Five micrograms of pGLY2988 digested with restriction enzyme Spe1 which cuts in the TRP2 targeting region were used to transform strain yGLY22-1. Strain yGLY22-1 (och1Δ::lacZ bmt2Δ::lacZ/KlMNN2-2/mnn4L1Δ::lacZ/MmSLC35A3 pnol Δmnn4Δ::lacZ met16Δ::lacZ), was constructed using methods described earlier (Nett and Gemgross, Yeast 20:1279 (2003); Choi et al., PNAS USA 100:5022 (2003); Hamilton et al., Science 301: 1244 (2003)).

Transformation of yGLY22-1 performed essentially as follows: YGLY22-1 was grown in 50 mL YPD media (yeast extract (1%), peptone (2%), dextrose (2%)) overnight to an OD of between about 0.2 to 6; After incubation on ice for 30 minutes, cells were pelleted by centrifugation at 2500-3000 rpm for 5 minutes. Media was removed and the cells washed three times with ice cold sterile 1M sorbitol before resuspension in 0.5 ml ice cold sterile 1M sorbitol. Ten μL of linearized DNA (10 ug) and 100 μL cell suspension was combined in an electroporation cuvette and incubated for 5 minutes on ice. Electroporation was in a Bio-Rad GenePulser Xcell following the preset *Pichia pastoris* protocol (2 kV, 25 μF, 200Ω), immediately followed by the addition of 1 mL YPDS recovery media (YPD media plus 1 M sorbitol). The transformed cells were allowed to recover for four hours to overnight at room temperature (26° C.) before plating the cells on the selective media. Following selection on media containing zeocin, transformants were screened by small scale expression analysis to detect anti-Her2 expression. Strain yGLY4280 was selected based on high level anti-Her2 expression.

Anti-Her2 protein expression for strain yGLY4280 was carried out in shake flasks at 24° C. with buffered glycerol-complex medium (BMGY) consisting of 1% yeast extract, 2% peptone, 100 mM potassium phosphate buffer pH 6.0, 1.34% yeast nitrogen base, 4×10-5% biotin, and 1% glycerol. The induction medium for protein expression was buffered methanol-complex medium (BMMY) consisting of 1% methanol instead of glycerol in BMGY. Pmt inhibitors in 100% methanol were added to the growth medium to a final concentration of 0.15 ug/mL at the time the induction medium was added. This is an intermediate dose that is sufficient to reduce O-glycosylation to roughly 50% of that observed without Pmt inhibitor treatment, and thus allows a comparison of potency for the different inhibitors. Following 24 hr further growth in the induction media, cultures were harvested and centrifuged at 2,000 rpm for five minutes to remove cells from the supernatant.

O-glycan determination was performed using a Dionex-HPLC(HPAEC-PAD) as follows. To measure O-glycosylation reduction, protein was purified from the growth medium using protein A chromatography (Li et al. Nat. Biotechnol. 24(2):210-5 (2006)) and the O-glycans released from and separated from protein by alkaline elimination (beta-elimination) (Harvey, Mass Spectrometry Reviews 18: 349-451 (1999)). This process also reduces the newly formed reducing terminus of the released O-glycan (either oligomannose or mannose) to mannitol. The mannitol group thus serves as a unique indicator of each O— glycan. 0.5 nmole or more of protein, contained within a volume of 100 μL PBS buffer, was required for beta elimination. The sample was treated with 25 μL alkaline borohydride reagent and incubated at 50° C. for 16 hours. About 20 uL arabitol internal standard was added, followed by 10 μL glacial acetic acid. The sample was then centrifuged through a Millipore filter containing both SEPA-BEADS and AG 50W-X8 resin and washed with water. The samples, including wash, were transferred to plastic autosampler vials and evaporated to dryness in a centrifugal evaporator. 150 μL 1% AcOH/MeOH was added to the samples and the samples evaporated to dryness in a centrifugal evaporator. This last step was repeated five more times. 200 μL of water was added and 100 μL of the sample was analyzed by high pH anion-exchange chromatography coupled with pulsed electrochemical detection-Dionex HPLC(HPAEC-PAD). Average O-glycan occupancy was determined based upon the amount of mannitol recovered.

The results are summarized in Table 1, which shows that the four novel Pmt inhibitors, Examples 1 to 4, reduce O-glycosylation to levels lower that that observed with Pmt inhibitor Pmti-3 as described in Orchard et al. (Bioorgan & Med Chem Letters (2004) 14:3975-3978) and patent publications by the same authors, including EP 1313471 B1 and Bobrowicz et al., U.S. Published Application No. 2007061631. Pmti-3 has the following chemical structure:

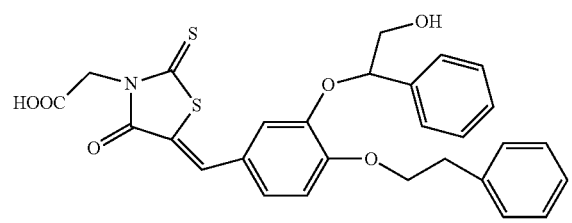 [SMILES: O=C(O)CN1C(=O)/C(=C/c2ccc(OCCc3ccccc3)c(OC(CO)c3ccccc3)c2)SC1=S]

TABLE 1

| Inhibitor (0.15 ug/mL) | O-glycan occupancy (moles O-mannose/moles Ab) |
| --- | --- |
| none | >14.0 |
| Pmti-3 | 8.1 |
| Example 1 | 4.1 |
| Example 2 | 4.3 |
| Example 3 | 5.5 |
| Example 4 | 5.2 |

Figure 1B:
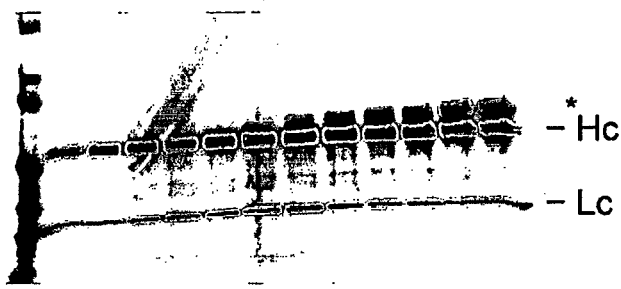
Figure 1C:
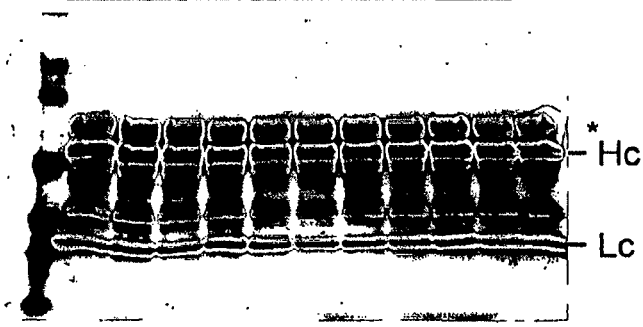

Visual proof that the novel Pmt inhibitors effectively reduce O-glycosylation of *Pichia*-produced recombinant protein is provided by FIG. 1, which shows the effects of increasing amounts of Pmt inhibitors on O-glycosylation of anti-Her2 heavy chain (Hc). Strain yGLY4280 was inoculated into 96-well deep well plates (Qiagen, Valencia, Calif.) containing 0.5 ml of BMGY media per well. After 24 hours growth with vigorous shaking, the 96-well plate was centrifuged at 2,000 rpm for five minutes to pellet cells. The media was removed and, following a wash step with 0.5 mL of BMMY media, the cells resuspended in 0.2 mL BMMY media in which Pmt inhibitors were diluted 2-fold across the rows (11 wells). Well #1 contained 5 ug/mL of inhibitor, well #2 contained 2.5 ug/mL and so on until well #10 contained 0.009 ug/mL; well #11 contained no inhibitor. After an additional 24 hours growth with vigorous shaking, the plate was centrifuged at 2,000 rpm for five minutes to pellet cells, and the cleared supernatant subjected to Western blot analysis to detect anti-Her2 expression. The Western blotting was performed as follows: seven μL of the supernatants were separated by reducing polyacrylamide gel electrophoresis (SDS-PAGE) according to Laemmli, U. K. (1970) Nature 227, 680-685 and then electroblotted onto nitrocellulose membranes (Schleicher & Schuell, now Whatman, Inc., Florham Park, N.J.). Anti-Her2 antibody chains were detected on the Western blots using a peroxidase-conjugated anti-human Hc and Lc antibody (Calbiochem/EMD Biosciences, La Jolla, Calif.) and developed using the ImmunoPure Metal Enhanced DAB Substrate Kit (Pierce Biotechnology, Rockford, Ill.). FIG. 1 shows the results of one such analysis in which the novel Pmt inhibitor from Example 4 (EX. 4, panel A) was tested against. Pmti-3 from Orchard et al. (panel B) and also an inactive compound as a control (panel C). As shown in panels A and B, Example 4 and Pmti-3 effectively reduced O-glycosylation of anti-Her2 Hc at concentrations as low as 0.018 ug/mL. In contrast, the inactive control compound (panel C) showed no reduction in Hc O-glycosylation. Similar results were obtained with inhibitors shown in Examples 1, 2, and 3. Taken together, these results indicate that the novel Pmt inhibitors shown in Examples 1 to 4 are effective inhibitors of fungal O-glycosylation.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A compound represented by the following structural formula:

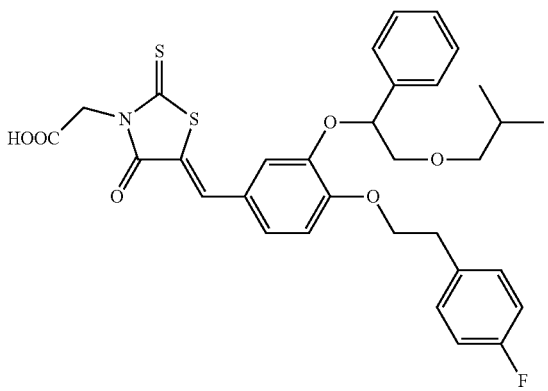 [SMILES: CC(C)COCC(Oc1cc(/C=C2\SC(=S)N(CC(=O)O)C2=O)ccc1OCCc1ccc(F)cc1)c1ccccc1]

or a salt thereof.

2. A method of producing a protein having reduced O-linked glycosylation comprising:
   (a) growing a cell in a culture that produces the protein;
   (b) contacting the culture with the compound of claim 1, which inhibit Pmt-mediated O-linked glycosylation; and
   (c) isolating the protein produced by the host cell.

3. The method of claim 2 wherein the culture of the cell is provided by:
   (a) providing a nucleic acid encoding a protein; and
   (b) introducing the nucleic acid into the cell.

4. The method of claim 3 wherein the culture is grown for a time sufficient to provide a multiplicity of the cells having the nucleic acid before contacting the culture with any of the one or more compounds which inhibit Pmt-mediated O-linked glycosylation.

5. The method of claim 3 wherein the culture is grown in the presence of any of the one or more compounds which inhibit Pmt-mediated O-linked glycosylation.

6. The method of claim 3 wherein the nucleic acid is operably linked to an inducible promoter.

7. The method of claim 6 wherein the culture is grown for a time sufficient to provide a multiplicity of the cells having the nucleic acid before contacting the culture with the one or more compounds which inhibit Pmt-mediated O-linked glycosylation and an inducer of the promoter to induce expression of the protein and isolating the protein produced by the cell in the presence of the one or more inhibitors and the inducer to produce the protein having reduced O-linked glycosylation.

8. The method of claim 6 wherein the culture is contacted with an inducer of the promoter to induce expression of the protein for a time before contacting the culture with the one or more compounds which inhibit Pmt-mediated O-linked glycosylation and isolating the protein produced by the cell in the presence of the one or more compounds which inhibit Pmt-mediated O-linked glycosylation and the inducer to produce the protein having reduced O-linked glycosylation.

9. The method of claim 3, wherein the cell is a fungal cell.

10. The method of claim 3, wherein the cell is a yeast cell.

11. The method of claim 3, wherein the cell is selected from the group consisting of *K. lactis, Pichia pastoris, Pichia methanolica*, and *Hansenula*.

12. The method of claim 3, wherein the cell is *Pichia pastoris*.

13. The method of claim 3, wherein the cell is a yeast or filamentous fungal cell that has been genetically modified to produce glycoproteins with a predominant N-glycan glycoform.

14. The method of claim 3 wherein the cells have been genetically modified to produce glycoproteins in which the N-glycosylation pattern is human-like or humanized.

15. The method of claim 3 wherein the protein is produced at a yield of at least 100 mg/liter of culture medium.

* * * * *

SEQUENCE LISTING

<160> NUMBER OF SEQ ID NOS: 6

<210> SEQ ID NO 1
<211> LENGTH: 57
<212> TYPE: DNA
<213> ORGANISM: Artificial Sequence
<220> FEATURE:
<223> OTHER INFORMATION: DNA encoding alpha-mating factor pre-signal peptide

<400> SEQUENCE: 1

```
atgagattcc catccatctt cactgctgtt ttgttcgctg cttcttctgc tttggct       57
```

<210> SEQ ID NO 2
<211> LENGTH: 19
<212> TYPE: PRT
<213> ORGANISM: Artificial Sequence
<220> FEATURE:
<223> OTHER INFORMATION: alpha-mating factor pre-signal peptide

<400> SEQUENCE: 2

Met Arg Phe Pro Ser Ile Phe Thr Ala Val Leu Phe Ala Ala Ser Ser
1               5                   10                  15

Ala Leu Ala

<210> SEQ ID NO 3
<211> LENGTH: 1353
<212> TYPE: DNA
<213> ORGANISM: Artificial Sequence
<220> FEATURE:
<223> OTHER INFORMATION: DNA encoding Anti-Her2 Heavy chain

<400> SEQUENCE: 3

```
gaggttcagt tggttgaatc tggaggagga ttggttcaac tggtggttc tttgagattg       60
tcctgtgctg cttccggttt caacatcaag gacacttaca tccactgggt tagacaagct     120
ccaggaaagg gattggagtg ggttgctaga atctacccaa ctaacggtta cacaagatac     180
gctgactccg ttaagggaag attcactatc tctgctgaca cttccaagaa cactgcttac     240
ttgcagatga actccttgag agctgaggat actgctgttt actactgttc cagatggggt     300
ggtgatggtt tctacgctat ggactactgg ggtcaaggaa cttttggtta ctgttttctcc    360
gcttctacta agggaccatc tgttttccca ttggctccat cttctaagtc tacttccggt     420
ggtactgctg ctttgggatg tttggttaaa gactacttcc cagagccagt tactgttttct    480
tggaactccg gtgcttttgac ttctggtgtt cacactttcc cagctgtttt gcaatcttcc    540
ggtttgtact ctttgtcctc cgttgttact gttccatcct cttccttggg tactcagact    600
tacatctgta acgttaacca caagccatcc aacactaagg ttgacaagaa ggttgagcca    660
aagtcctgtg acaagactca tacttgtcca ccatgtccag ctccagaatt gttgggtggt    720
ccttccgttt ttttgttccc accaaagcca aggacactt tgatgatctc agaactcca     780
gaggttacat gtgttgttgt tgacgttttct cacgaggacc cagaggttaa gttcaactgg    840
tacgttgacg gtgttgaagt tcacaacgct aagactaagc caagagagga gcagtacaac    900
tccacttaca gagttgtttc cgttttgact gttttgcacc aggattggt gaacggaaag    960
gagtacaagt gtaaggttttc caacaaggct tgccagctc aatcgaaaa gactatctcc   1020
aaggctaagg gtcaaccaag agagccacag gtttacactt tgccaccatc agagatgag   1080
ttgactaaga accaggtttc cttgacttgt ttggttaagg gattctaccc atccgacatt    1140
gctgttgaat gggagtctaa cggtcaacca gagaacaact acaagactac tccacctgtt   1200
```

-continued

```
ttggactctg acggttcctt tttcttgtac tccaagttga ctgttgacaa gtccagatgg   1260
caacagggta acgttttctc ctgttccgtt atgcatgagg ctttgcacaa ccactacact   1320
caaaagtcct tgtctttgtc ccctggtaag taa                                1353
```

```
<210> SEQ ID NO 4
<211> LENGTH: 450
<212> TYPE: PRT
<213> ORGANISM: Artificial Sequence
<220> FEATURE:
<223> OTHER INFORMATION: Anti-Her2 Heavy chain

<400> SEQUENCE: 4
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 5
<211> LENGTH: 645
<212> TYPE: DNA
<213> ORGANISM: Artificial Sequence
<220> FEATURE:
<223> OTHER INFORMATION: DNA encoding Anti-Her2 Light chain

<400> SEQUENCE: 5
gacatccaaa tgactcaatc cccatcttct ttgtctgctt ccgttggtga cagagttact      60
atcacttgta gagcttccca ggacgttaat actgctgttg cttggtatca acagaagcca     120
ggaaaggctc caaagttgtt gatctactcc gcttccttct tgtactctgg tgttccatcc     180
agattctctg gttccagatc cggtactgac ttcactttga ctatctcctc cttgcaacca     240
gaagatttcg ctacttacta ctgtcagcag cactacacta ctccaccaac tttcggacag     300
ggtactaagg ttgagatcaa agaactgttg ctgctccat ccgttttcat tttcccacca     360
tccgacgaac agttgaagtc tggtacagct tccgttgttt gtttgttgaa caacttctac     420
ccaagagagg ctaaggttca gtggaaggtt gacaacgctt tgcaatccgg taactcccaa     480
gaatccgtta ctgagcaaga ctctaaggac tccacttact ccttgtcctc cactttgact     540
ttgtccaagg ctgattacga aagcacaag gtttacgctt gtgaggttac acatcagggt     600
ttgtcctccc cagttactaa gtccttcaac agaggagagt gttaa                    645

<210> SEQ ID NO 6
<211> LENGTH: 213
<212> TYPE: PRT
<213> ORGANISM: Artificial Sequence
<220> FEATURE:
<223> OTHER INFORMATION: Anti-Her2 Light chain

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

| | | | | | | | | | | | | | | |
|---|---|---|---|---|---|---|---|---|---|---|---|---|---|---|
| Ser 65 | Arg | Ser | Gly | Thr 70 | Asp | Phe | Thr | Leu | Thr 75 | Ile | Ser | Ser | Leu | Gln 80 | Pro |
| Glu | Asp | Phe | Ala | Thr 85 | Tyr | Tyr | Cys | Gln | Gln 90 | His | Tyr | Thr | Thr | Pro 95 | Pro |
| Thr | Phe | Gly | Gln 100 | Gly | Thr | Lys | Val | Glu 105 | Ile | Lys | Arg | Thr | Val 110 | Ala | Ala |
| Pro | Ser | Val 115 | Phe | Ile | Phe | Pro | Pro 120 | Ser | Asp | Glu | Gln | Leu 125 | Lys | Ser | Gly |
| Thr | Ala 130 | Ser | Val | Val | Cys | Leu 135 | Asn | Asn | Phe | Tyr | Pro 140 | Arg | Glu | Ala | Lys |
| Val 145 | Gln | Trp | Lys | Val | Asp 150 | Asn | Ala | Leu | Gln | Ser 155 | Gly | Asn | Ser | Gln | Glu 160 |
| Ser | Val | Thr | Glu | Gln 165 | Asp | Ser | Lys | Asp | Ser 170 | Thr | Tyr | Ser | Leu | Ser 175 | Ser |
| Thr | Leu | Thr | Leu 180 | Ser | Lys | Ala | Asp | Tyr 185 | Glu | Lys | His | Lys | Val 190 | Tyr | Ala |
| Cys | Glu | Val 195 | Thr | His | Gln | Gly | Leu 200 | Ser | Ser | Pro | Val | Thr 205 | Lys | Ser | Phe |
| Asn | Arg | Gly 210 | Glu | Cys | | | | | | | | | | | |